United States Patent [19]

Smith et al.

[11] 4,231,951

[45] Nov. 4, 1980

[54] COMPLEX SALT PHOTOINITIATOR

[75] Inventors: George H. Smith, Maplewood; Peter M. Olofson, North Saint Paul, both of Minn.

[73] Assignee: Minnesota Mining and Manufacturing Company, Saint Paul, Minn.

[21] Appl. No.: 51,901

[22] Filed: Jun. 25, 1979

Related U.S. Application Data

[62] Division of Ser. No. 876,114, Feb. 8, 1978, Pat. No. 4,173,476.

[51] Int. Cl.$^3$ .............................................. C07F 9/90
[52] U.S. Cl. .................................................... 260/446
[58] Field of Search ........................................ 260/446

[56] References Cited

U.S. PATENT DOCUMENTS

| | | | |
|---|---|---|---|
| 3,585,227 | 6/1971 | Dreyfuss | 260/446 X |
| 3,850,857 | 11/1974 | Dreyfuss | 260/446 X |
| 3,981,897 | 9/1976 | Crivello | 260/446 X |
| 4,058,400 | 11/1977 | Crivello | 260/440 X |
| 4,069,055 | 1/1978 | Crivello | 260/446 X |
| 4,136,102 | 1/1979 | Crivello | 260/446 X |
| 4,161,478 | 7/1979 | Crivello | 260/446 X |

*Primary Examiner*—Helen M. S. Sneed
*Attorney, Agent, or Firm*—C. Alexander; D. M. Sell; D. P. Edmundson

[57] ABSTRACT

A triarylsulfonium complex salt is described which has particular utility as a photoinitiator for the polymerization of epoxide monomers in thick films or coatings. Photopolymerizable compositions are also described.

4 Claims, No Drawings

COMPLEX SALT PHOTOINITIATOR

This is a division of application Ser. No. 876,114 filed Feb. 8, 1978, now U.S. Pat. No. 4,173,476.

BACKGROUND OF THE INVENTION

This invention relates to photopolymerizable (i.e. photohardenable) compositions. More particularly, this invention relates to complex salt photoinitiators useful in such compositions.

One-part photocurable epoxide compositions containing a diaryliodonium complex salt photoinitiator have been previously described. One-part photocurable compositions containing a triarylsulfonium complex salt photoinitiator have also been previously described (e.g. in assignee's copending applications Ser. Nos. 609,897 and 609,898, filed Sept. 2, 1975, and in U.S. Pat. No. 4,069,054, all incorporated herein by reference). Such compositions have commercial utility for many applications such as protective coatings for wood, metal, paperboard, floor tile, lithographic printing plates, printing inks, circuit board solder masks, etc. Such protective coatings are typically thin films of about 0.1 to 3 mils (e.g. 0.002 to 0.08 millimeters) that rapidly photocure when exposed to light.

The above-described compositions are 100% solids (i.e. they do not contain volatile non-reactive solvents). Consequently, such compositions are of major importance in eliminating air pollution and gas drying ovens which are very energy-consumptive.

There are many potential applications for curable compositions in the form of thick films or coatings, e.g. encapsulation of electronic components, reinforced plastics, relief printing plates, autobody repair, and sealants. In such applications the composition must be capable of curing rapidly to thicknesses up to one-half inch (approximately 1.3 centimeters) or more. The photocurable compositions described hereinbefore have not been known to exhibit such thick cure capability.

SUMMARY OF THE INVENTION

In accordance with the present invention there is provided a triarylsulfonium complex salt of the formula:

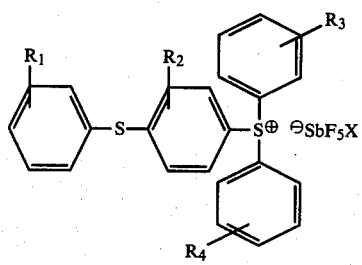

where X is F or OH; $R_1$, $R_2$, $R_3$ and $R_4$ are each selected from H, lower alkyl, alkoxy, or halogen. It has been unexpectedly found that these complex salts are effective as photoinitiators for the polymerization of epoxide compositions in thick films (e.g. up to about one-half inch in thickness).

DETAILED DESCRIPTION OF THE INVENTION

The novel triarylsulfonium complex salts of the invention are of the formula

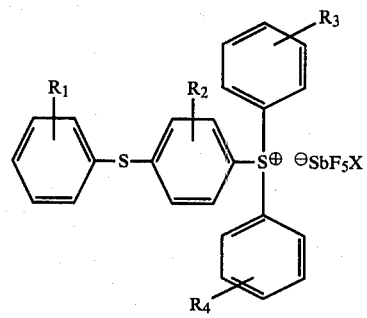

where X is F or OH; $R_1$, $R_2$, $R_3$ and $R_4$ are each selected from H, lower alkyl (i.e. up to about 4 carbons), alkoxy (containing up to about 4 carbons), or halogen.

The photopolymerizable compositions of the invention comprise an epoxide monomer and a small amount of the triarylsulfonium complex salt described above. The particular amount of complex salt required to be present is dependent upon the thickness of the coating to be cured, the intensity of the light used to cure the coating, the type of substrate being coated, the type of monomer present, and whether the coating is heated at the time it is exposed to light. Generally speaking, the complex salt is present in an amount of 0.02% to 1.5% by weight based on the weight of the epoxide monomer. Preferably, the complex salt is present in an amount of about 0.03 to 1.25% by weight based on the weight of the epoxide monomer.

Although the novel complex salts described above are particularly useful in the curing of thick films or coatings of epoxide compositions, such salts are also useful in the curing of normally thin films of epoxide compositions. However, it has been found that an inverse correlation exists between the concentration of the salt in the composition and the thickness to which such composition polymerizes or hardens upon exposure to a given light intensity.

Epoxy-containing materials useful in the compositions of the invention are any organic compounds having an oxirane ring

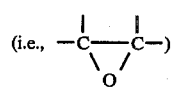

polymerizable by ring opening. Such materials, broadly called epoxides, include monomeric epoxy compounds and epoxides of the polymeric type and can be aliphatic, cycloaliphatic, or aromatic. These materials generally have, on the average, at least one polymerizable epoxy groups per molecule (preferably two or more epoxy groups per molecule). The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The molecular weight of the epoxy-containing materials may vary from 58 to about 100,000 or more. Mixtures of various epoxy-containing materials can also be used in the compositions of this invention.

Useful epoxy-containing materials include those which contain cyclohexene oxide groups such as the epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, incorporated herein by reference.

Further epoxy-containing materials which are particularly useful in the practice of this invention include glycidyl ether monomers of the formula

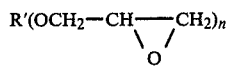

where R' is alkyl or aryl and n is an integer of 1 to 6. Examples are the glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type which can be used in the practice of this invention are described in U.S. Pat. No. 3,018,262, incorporated herein by reference, and in "Handbook of Epoxy Resins" by Lee and Neville, McGraw-Hill Book Co., New York (1967).

There is a host of commercially available epoxy-containing materials which can be used in this invention. In particular, epoxides which are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4421" from Union Carbide Corp.), 3,4-epoxy-6-methylcyclohexylmethyl-3,4-epoxy-6-methylcyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.), aliphatic epoxy modified with polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, epoxy silanes (e.g., beta-(3,4-epoxycyclohexyl)ethyltrimethoxy silane and gamma-glycidoxypropyltrimethoxy silane, commercially available from Union Carbide), flame retardant epoxy resins (e.g., "DER-580", a brominated bisphenol type epoxy resin available from Dow Chemical Co.), 1,4-butanediol diglycidyl ether (e.g., "Araldite RD-2" from Ciba-Geigy), polyglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.

The epoxide compositions of the invention may also contain hydroxyl-containing material which is copolymerizable with the epoxide. The hydroxyl-containing material which is useful may be any liquid or solid organic material having hydroxyl functionality of at least 1, and preferably at least 2. Also, the hydroxyl-containing organic material is free of other "active hydrogens". The term "active hydrogen" is well known and commonly used in the art, and as used herein it means active hydrogen as determined by the method described by Zerewitinoff in J. Am. Chem. Soc., Vol. 49, 3181 (1927), incorporated herein by reference. Of course, the hydroxyl-containing material is also substantially free of groups which may be thermally or photolytically unstable; that is, the material will not decompose or liberate volatile components at temperatures below about 100° C. or in the presence of actinic light which may be encountered during the desired curing conditions for the photocopolymerizable composition.

Preferably the organic material contains two or more primary or secondary aliphatic hydroxyl groups (i.e., the hydroxyl group is bonded directly to a non-aromatic carbon atom). The hydroxyl groups may be terminally situated, or they may be pendent from a polymer or copolymer. The molecular weight (i.e., number average molecular weight) of the hydroxyl-containing organic material may vary from very low (e.g., 62) to very high (e.g., 20,000 or more). The equivalent weight (i.e., number average equivalent weight) of the hydroxyl-containing material is preferably in the range of about 31 to 5000. When materials of higher equivalent weights are used they tend to reduce the rate and extent of copolymerization.

Representative examples of suitable organic materials having a hydroxyl functionality of 1 include alkanols, monoalkyl ethers of polyoxyalkyleneglycols, monoalkyl ethers of alkyleneglycols, and others known to the art.

Representative examples of useful monomeric polyhydroxy organic materials include alkylene glycols (e.g., 1,2-ethanediol, 1,3-propanediol, 1,4-butanediol, 2-ethyl-1,6-hexanediol, bis(hydroxymethyl)cyclohexane, 1,18-dihydroxyoctadecane, 3-chloro-1,2-propanediol), polyhydroxyalkanes (e.g., glycerine, trimethylolethane, pentaerythritol, sorbitol), and other polyhydroxy compounds such as N,N-bis(hydroxyethyl)benzamide, 2-butyne-1,4-diol, 4,4'-bis(hydroxymethyl)diphenylether, castor oil, etc.

Representative examples of useful polymeric hydroxy-containing materials include polyoxyethylene and polyoxypropylene glycols and triols of molecular weights from about 200 to about 10,000, corresponding to equivalent weights of 100 to 5000 for the diols or 70 to 3300 for triols; polytetramethylene glycols of varying molecular weight; hydroxy-terminated polyesters and hydroxy-terminated polylactones; and hydroxy-terminated polyalkadienes.

Useful commercially available hydroxyl-containing materials include the "Polymeg" ® series (available from Quaker Oats Company) of polytetramethylene ether glycols such as "Polymeg" 650, 1000 and 2000; "PeP" series (available from Wyandotte Chemicals Corporation) of polyoxyalkylene tetrols having secondary hydroxyl groups such as "PeP" 450, 550 and 650; "PCP" series (available from Union Carbide) of polycaprolactone polyols such as "PCP" 0200, 0210, 0230, 0240, 0300; "Paraplex U-148" (available from Rohm and Haas), an aliphatic polyester diol; "Multron" ® series (available from Mobay Chemical Co.) of saturated polyester polyols such as "Multron" R-2, R-12A, R-16, R-18, R-38, R-68 and R-74.

The amount of hydroxyl-containing organic material which may be used in the compositions of the invention may vary over broad ranges, depending upon factors such as the compatibility of the hydroxyl-containing material with the epoxide, the equivalent weight and functionality of the hydroxyl-containing material, the physical properties desired in the final cured composition, the desired speed of photocure, etc.

Generally speaking, with increasing amounts of hydroxyl-containing material in the composition the cured product exhibits improved impact resistance, adhesion to substrates, flexibility, and decreased shrinkage during curing, and correspondingly there is a gradual decrease in hardness, tensile strength and solvent-resistance.

Although both mono-functional and poly-functional hydroxyl-containing materials provide desirable results in the compositions of the invention, use of the poly-functional hydroxyl-containing materials is highly preferred for a majority of applications, although the mono-functional hydroxyl-containing materials are particularly effective in providing low viscosity, solvent-free coating compositions. When using hydroxyl-containing organic materials having a functionality significantly less than 2 (e.g., 1 to 1.5), amounts greater than about 0.4 equivalent of hydroxyl per equivalent of epoxy tend to provide cured compositions which are generally low in internal strength and tensile strength and are susceptible to solvent attack, and consequently may be unsuitable for many applications. This tendency becomes increasingly more apparent with increasing equivalent weight of the hydroxyl-containing material. Accordingly, when using mono-functional hydroxy materials it is preferred that the equivalent weight thereof be no greater than about 250.

When poly-functional hydroxyl-containing material is used it may be used in any amount, depending upon the properties desired in the cured composition. For example, the ratio of equivalents of hydroxyl-containing material to equivalents of epoxide may vary from about 0.001/1 to 10/1.

Mixtures of hydroxyl-containing materials may be used, when desired. For example, one may use mixtures of two or more poly-functional hydroxy materials, one or more mono-functional hydroxy materials with poly-functional hydroxy materials, etc.

The complex salts of this invention can be prepared using conventional techniques described in the literature. For example, the procedure to prepare

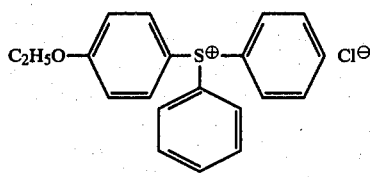

described by Smiles and Le Rossignol and J. Chem. Soc., 696 (1906) with some modifications provides a versatile technique of broad applicability. For example, one useful technique for making the desired product directly is as follows:

To a 100 ml. flask fitted with a reflux condenser is added 20.2 grams of diphenylsulfoxide, 20.5 grams diphenylsulfide and 19.9 grams of phosphorous pentoxide. This mixture is heated on a steam bath for three hours. The reaction mixture is then transferred portionwise to 2500 ml. of stirred hot water. The slightly hazy solution is allowed to cool, decanted from a small amount of insoluble oil and filtered through a bed of filter aid. To the clear filtrate is added, with stirring, 25.9 grams powdered $NaSbF_6$. The product separates as a viscous oil; the water layer is decanted. The oil layer is then dissolved in 400 ml. of $CH_2Cl_2$, dried, and the solvent removed under vacuum to give 26.7 grams of

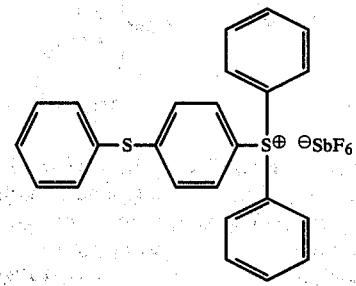

in 44% yield. Crystallization from isopropanol provides analytically pure material; melting point 118°–119° C. Analysis of the pure product is as follows:

|  | Theoretical | Experimental |
| --- | --- | --- |
| % C | 47.5 | 47.4 |
| % H | 3.1 | 3.0 |

This procedure will provide the desired substituted derivative by using the appropriately substituted diphenylsulfoxide and diphenylsulfide.

The preferred and more economical method of preparation of the chloride is by means of the procedure described in U.S. Pat. No. 2,807,648, incorporated herein by reference. Contrary to the results described in the patent, surprisingly, we have found that a mixture of aryl sulfonium chlorides results when benzene is used as a starting material as in Examples 1 and 10 of such patent. This mixture contains the desired

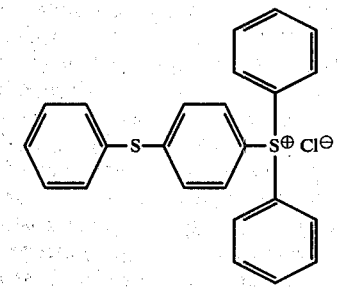

in concentrations as high as 55%. Other components in the mixture are $\phi_3S^\oplus Cl^\ominus$ and $(R\phi)_3S^\oplus Cl^\ominus$ where R is H and Cl. This mixture is designated herein as $Ar_3SCl$. Following the procedure of Example 10 of the above patent, one obtains an aqueous solution of $Ar_3SCl$. Its concentration is determined by analysis and then diluted with additional water to obtain a 25% by weight solution. To a stirred 25% aqueous solution of $Ar_3SCl$ is added an equimolar amount of solid $NaSbF_6$ or $KSbF_6$. The solids are added as a powder stream with stirring.

The product precipitates and is filtered and dried to give quantitative yields from the chloride.

To prepare the corresponding

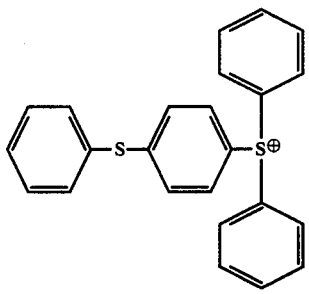

$SbF_5OH^{\ominus}$ and $Ar_3SSbF_5OH$ the $NaSbF_6$ is first dissolved in water in which it spontaneously hydrolyzes to $NaSbF_5OH$ and $HF$. This solution is then added to the aqueous solution of the chloride in the above examples. Infrared analysis readily distinguishes between $SbF_6$ and $SbF_5OH$. The Sb-F stretch absorption for $SbF_6$ occurs at 655 $cm^{-1}$ and for $SbF_5OH$ shifts to 630 $cm^{-1}$.

The amount of

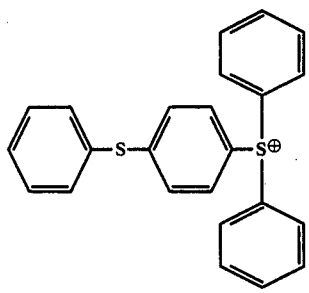

$SbF_6^{\ominus}$ present in the product mixture can readily be determined by UV absorption. The compounds of this invention have a characteristic absorption peak at 308 nm in $CH_2Cl_2$. The absorptivity of this compound is 41.0. The absorptivity of a conventional mixture such as obtained from the above procedure averages about 19.6. The concentration of the desired product is therefore 48%. This mixture is designated as $Ar_3SSbF_6$ in the examples and has good photoinitiating activity.

The addition of a small amount of heat either prior to the exposure or during the exposure of the compositions significantly increases the rate of cure of the epoxide monomers when using the photoinitiators of this invention. This is not true when one uses the corresponding $AsF_6$, $BF_4$ or $PF_6$ metal halide complex salts. A lower intensity UV lamp such as a sunlamp can be effectively used since it also provides heat. The heat apparently accelerates the rate of polymerization of the epoxide by the $HSbF_6$ acid that is formed by photolysis of the sulfonium salt. Surprisingly, this apparently does not occur with the $AsF_6$, $PF_6$ or $BF_4$ acids.

The photopolymerizable compositions of this invention are particularly suitable in applications where a thick film or coating must be obtained. For example, these compositions have particular utility as potting resins for the potting, sealing or encapsulation of electronic components, optical lenses, industrial sealants, autobody and boat repair, molds, shock absorbing materials, fiber reinforced plastics, protective coatings, patching materials, etc.

It is permissible and oftentimes advantageous to include in the photopolymerizable compositions various fillers (e.g., silica, talc, glass bubbles, clays, starch, finely ground rubber, etc.) up to 50% or more, slip agents, viscosity modifiers, tackifying agents, micro fibers, and so forth. The photopolymerizable compositions can be applied to various substrates such as plastic, metal, wood, concrete, glass, paper, ceramic, etc.

Photopolymerization of the compositions of the invention occurs upon exposure to any source of radiation emitting actinic radiation in the ultraviolet region of the spectrum (e.g. 1840 A to 4000 A). Suitable sources of radiation include mercury vapor discharge, lamps, carbon arc, xenon, sunlight, etc. The amount of exposure is dependent upon such factors as concentration of photoinitiator, chemical structure of the monomer and its equivalent weight, thickness of coating, type of substrate, intensity of lamp, and the amount of heat absorbed by the coating or the substrate on which it is disposed.

EXAMPLES 1-8

The following examples show the effect of the cationic portion of the onium photoinitiator for thick film curing.

Solutions were prepared containing 100 parts of aromatic glycidyl ether epoxide monomer DER-332 (Dow Chemical Company) and 0.1 parts of the sulfonium salts listed in Table I. Each solution was weighed into a black rubber mold to give a sample thickness of 200 mils. The mold was then placed under a 275 W GE sunlamp at a distance of 4 inches. Each sample was exposed as indicated, immersed in acetone, air dried and its thickness measured and recorded in Table I.

Table I

| Example | Onium Salt | Exp. (min) | Thickness (mils) |
|---|---|---|---|
| 1 | $\phi S\phi S\ (\phi)_2\ SbF_6$ | 3 | 200 |
| 2 | $Ar_3S\ SbF_6$ | 5 | 200 |
| 3 | $\phi O\phi S\ (\phi)_2\ SbF_6$ | 15 | 10-20 |
| 4 | $C_2H_5O\phi S\ (\phi)_2\ SbF_6$ | 15 | 30-40 |
| 5 | $(Cl-\phi)_3S\ SbF_6$ | 15 | 30-40 |
| 6 | $\phi_3S\ SbF_6$ | 15 | 40-50 |
| 7 | $\phi_2I\ SbF_6$ | 15 | 45-50 |
| 8 | $CH_3\phi_2I\ SbF_6$ | 15 | 45-50 |

EXAMPLES 9-18

The following examples show the effect of the anionic portion of the sulfonium photoinitiator for thick film curing.

Solutions were prepared containing 100 parts of epoxide ERL-4221 (Union Carbide) and 0.1 parts of the sulfonium salts listed in Table II. Each solution was weighed into a black rubber mold to give a sample thickness of 200 mils. The mold was then placed under a 275 W GE sunlamp at a distance of 4 inches. Each sample was exposed for 4 min. and 15 min. If cured, the sample was then removed, immersed in acetone and stirred for 20 min., removed, air dried, and its thickness measured and recorded in Table II.

Table II

| | | Thickness in mils | |
|---|---|---|---|
| Example | Sulfonium Salts | 4 min. exp. | 15 min. exp. |
| 9 | $\phi S\phi S\ (\phi)_2\ SbF_6$ | 200 | |
| 10 | $Ar_3S\ SbF_6$ | 200 | |

Table II-continued

| Example | Sulfonium Salts | Thickness in mils | |
|---|---|---|---|
| | | 4 min. exp. | 15 min. exp. |
| 11 | $Ar_3S$ $SbF_5OH$ | 175 | |
| 12 | $\phi S\phi S$ $(\phi)_2$ $SbF_5OH$ | 200 | |
| 13 | $\phi S\phi S$ $(\phi)_2$ $PF_6$ | 0 | 0 |
| 14 | $\phi S\phi S$ $(\phi)_2 BF_4$ | 0 | 0 |
| 15 | $\phi S\phi S$ $(\phi)_2$ $AsF_6$ | 0 | 0 |
| 16 | $Ar_3S$ $PF_6$ | 0 | 0 |
| 17 | $Ar_3S$ $AsF_6$ | 0 | 0 |
| 18 | $Ar_3S$ $BF_4$ | 0 | 0 |

EXAMPLES 19–24

The photoinitiators of the present invention can also be used to cure thick coatings of aliphatic glycidyl ethers to give rubberlike products. The following sulfonium salts in the indicated concentrations by weight were dissolved in epoxide monomer DER-736 (Dow Chemical Company) and exposed 4.5 mins. in a rubber mold to a 275 W GE sunlamp at a distance of 4 inches. The thickness of the cured polymer was measured after acetone immersion.

| Example | Sulfonium Salt | Wt. % Conc. | Thickness in mils |
|---|---|---|---|
| 19 | $\phi S\phi S(\phi)_2$ $SbF_6$ | 0.1 | 220 |
| 20 | $Ar_3S$ $SbF_6$ | 0.5 | 220 |
| 21 | $Ar_3S$ $AsF_6$ | 0.5 | 0 |
| 22 | $\phi S\phi S(\phi)_2$ $PF_6$ | 0.5 | 0 |
| 23 | $Ar_3S$ $PF_6$ | 0.5 | 0 |
| 24 | $Ar_3S$ $BF_4$ | 0.5 | 0 |

EXAMPLES 25–35

The following comparative examples shows the preparation of photocured coatings of 500 mils in thickness using the photoinitiators of this invention and the inability of prior art photoinitiators. The cured coatings comprising a combination of epoxide monomer with a polyol provides elastomeric thick films useful as industrial sealants.

A master solution of 50 parts of ERL-4221 and 50 parts of polyethyleneglycol 400 was prepared. To 20 parts of this solution was added the indicated weight % of the photoiniator. The samples were poured into a rubber mold of 500 mils depth and exposed to a 275 W GE sunlamp at a distance of 4 inches. The following table shows the results.

| Example | Photoinitiator | % Conc. | Exp. Time (min.) | Thickness (mils) |
|---|---|---|---|---|
| 25 | $\phi S\phi S\phi_2$ $SbF_6$ | .05 | 5 | 500 |
| 26 | $Ar_3S$ $SbF_6$ | .05 | 6 | 500 |
| 27 | $\phi_3S$ $SbF_6$ | .05 | 15 | 0 |
| 28 | " | .25 | 6 | 20 |
| 29 | " | .25 | 15 | 40 |
| 30 | " | .50 | 6 | 50 |
| 31 | " | .50 | 15 | 60 |
| 32 | $\phi O\phi S\phi_2 SbF_6$ | .05 | 6 | 0 |
| 33 | " | .05 | 15 | 0 |
| 34 | naphthyl-$S\phi_2$ $SbF_6$ | .05 | 6 | 50 |
| 35 | " | .05 | 15 | 90 |

Corresponding $PF_6$, $AsF_6$, and $BF_4$ salts did not provide any significant curing.

What is claimed is:

1. The process for the preparation of a triarylsulfonium hexafluoroantimonate salt comprising the steps of
   (a) providing an aqueous solution of a watersoluble triarylsulfonium salt;
   (b) adding solid $NaSbF_6$ or $KSbF_6$ to said aqueous solution to form a mixture; and
   (c) recovering triarylsulfonium hexafluoroantimonate from said mixture.

2. The process of claim 1, wherein $NaSbF_6$ is used in step (b).

3. The process of claim 1, wherein $KSbF_6$ is used in step (b).

4. The process of claim 1, wherein the amount of $NaSbF_6$ or $KSbF_6$ added to said aqueous solution is equimolar with the amount of triarylsulfonium salt present in said solution.

* * * * *

UNITED STATES PATENT AND TRADEMARK OFFICE
CERTIFICATE OF CORRECTION

PATENT NO. : 4,231,951
DATED : November 4, 1980
INVENTOR(S) : George H. Smith and Peter M. Olofson It is certified that error appears in the above—identified patent and that said Letters Patent is hereby corrected as shown below:

Col. 3, line 44, "ERL 4421" should read -- ERL 4221 -- .

Signed and Sealed this

Seventh Day of April 1981

[SEAL]

Attest:

RENE D. TEGTMEYER

Attesting Officer     Acting Commissioner of Patents and Trademarks